United States Patent

Lashinski et al.

[11] Patent Number: 5,868,780
[45] Date of Patent: Feb. 9, 1999

[54] STENTS FOR SUPPORTING LUMENS IN LIVING TISSUE

[76] Inventors: Robert D. Lashinski, 409 Princess Way, Windsor, Calif. 95492; Matthew J. Birdsall, 2561 Barona Pl., Santa Rosa, Calif. 95405

[21] Appl. No.: 620,878

[22] Filed: Mar. 22, 1996

[51] Int. Cl.$^6$ .................................................. A61M 29/00
[52] U.S. Cl. .............................. 606/198; 606/191; 623/1; 623/12
[58] Field of Search .................................. 606/191, 192, 606/194, 195, 198; 623/1, 12

[56] References Cited

U.S. PATENT DOCUMENTS

| | | |
|---|---|---|
| 4,733,665 | 3/1988 | Palmaz . |
| 5,015,253 | 5/1991 | MacGregor ................................ 623/1 |
| 5,061,275 | 10/1991 | Wallsten et al. ............................ 623/1 |
| 5,064,435 | 11/1991 | Porter ...................................... 606/198 |
| 5,135,536 | 8/1992 | Hillstead . |
| 5,292,331 | 3/1994 | Boneau . |
| 5,360,443 | 11/1994 | Barone et al. ............................ 606/194 |
| 5,383,892 | 1/1995 | Cardon et al. ............................ 606/198 |
| 5,540,712 | 7/1996 | Kleshinski et al. ....................... 606/198 |
| 5,549,663 | 8/1996 | Cottone, Jr. .................................. 623/1 |
| 5,591,226 | 1/1997 | Trerotola et al. ............................ 623/1 |
| 5,609,627 | 3/1997 | Goicoechea et al. .................... 606/194 |

*Primary Examiner*—Michael Buiz
*Assistant Examiner*—Daphna Shai
*Attorney, Agent, or Firm*—Richard L. Klein

[57] ABSTRACT

A stent for helping to hold open a lumen in a tubular body structure has at least one axial portion (preferably an axial end portion) that stents the surrounding portion of the tubular body structure to a lesser degree than another axial portion of the stent. For example, the stent portion that stents to a lesser degree may be circumferentially weaker than the other stent portion, or it may recoil more than the other stent portion after the stent is applied by being circumferentially expanded and then released.

11 Claims, 1 Drawing Sheet

STENTS FOR SUPPORTING LUMENS IN LIVING TISSUE

BACKGROUND OF THE INVENTION

This invention relates to stents for supporting lumens in living tissue in order to help hold those lumens open. The lumen may be a blood vessel, a bile duct, or any other similar body conduit that is tending to improperly constrict as a result of disease or malfunction. The lumen may be a graft (whether natural or artificial) in any type of body conduit.

It is known to insert hollow tube-defining structures ("stents") into tubular body organs or structures such as blood vessels to help open and keep open those body structures. See Boneau U.S. Pat. No. 5,292,331 and Hillstead U.S. Pat. No. 5,135,536 for examples of metal stent structures. (These two references are hereby incorporated by reference herein.) Stents of these types are typically introduced into a blood vessel or other tubular body structure on the deflated balloon of a balloon catheter. When the stent is at the desired location in the tubular body structure, the balloon is inflated to circumferentially expand the stent. The balloon is then deflated and the catheter is withdrawn, leaving the circumferentially expanded stent in the tubular body structure, usually as a permanent prosthesis for helping to hold the tubular body structure open and prevent stenosis or restenosis of that body structure.

While stents and stent applications of the type described above have been found to work extremely well, there may be room for improvement (at least in some cases) in avoiding abrupt transitions between stented and unstented regions of a tubular body structure. Such abrupt transitions may trigger a body reaction at or near the transition. Avoiding abrupt transitions or reducing the abruptness of such transitions may therefore be more therapeutic.

In view of the foregoing, it is an object of this invention to provide improved structures and methods for stenting tubular body structures.

It is a more particular object of this invention to provide stent structures and methods which reduce the abruptness of the transitions between the stented region and the unstented regions in a tubular body structure in which the stent is employed.

SUMMARY OF THE INVENTION

These and other objects of the invention are accomplished in accordance with the principles of the invention by providing stent structures having at least one axial end portion which less strongly holds open or stents the surrounding portion of the tubular body structure in which the stent is being employed than a remaining portion of the stent holds open the portion of the tubular body structure that surrounds the remaining portion. Preferably both axial end portions of the stent are like the above-described end portion, with the above-described remaining portion being medial between the two axial end portions. The axial end portion or portions which less strongly hold open the tubular body structure can be provided in any of a large number of ways. For example, the axial end portion or portions can be made circumferentially weaker (elastically or plastically) than other portions of the stent. (As is explained in more detail below, terms like "plastic" and "plastically" are used herein to mean any type of non-elastic (e.g., permanent) deformation.) Or the axial end portion or portions can be made to recoil somewhat more after circumferential expansion and release than other portions of the stent recoil.

Methods of making stents in accordance with the invention include forming first and second axially spaced, annular stent portions so that the first portion is circumferentially stronger (elastically or plastically) than the second portion. Alternatively, the methods of making stents in accordance with the invention may include forming first and second axially spaced annular stent portions so that the second portion has a higher yield strength than the first portion. The first portion is preferably formed as an axially medial portion of the stent, while the second portion is preferably formed as an axial end portion of the stent. A third annular axial portion of the stent may be formed similarly to the second portion, and is preferably formed as another axial end portion of the stent that is axially remote from the second portion.

Methods of using stents in accordance with the invention include inserting the stent into a tubular body structure, circumferentially expanding the stent, and then releasing the stent so that the tubular body structure can circumferentially recompress a circumferentially weaker, second annular axial portion of the stent more than it recompresses a circumferentially stronger, first annular axial portion of the stent. The weaker portion can be elastically or plastically weaker than the stronger portion. Alternatively, methods of using stents in accordance with the invention include inserting the stent into a tubular body structure, circumferentially expanding the stent, and then releasing the stent so that a second annular axial portion of the stent which has a relatively high yield strength springs back more from circumferential expansion than a first annular axial portion of the stent which has a relatively low yield strength.

Further features of the invention, its nature and various advantages will be more apparent from the accompanying drawings and the following detailed description of the preferred embodiments.

BRIEF DESCRIPTION OF THE DRAWINGS

FIG. 1 shows the stent prior to circumferential expansion.

FIG. 3 shows the stent after circumferential expansion and implantation in a tubular body structure.

DETAILED DESCRIPTION OF THE PREFERRED EMBODIMENTS

The above-mentioned Boneau and Hillstead patents, and the references cited in those patents, make it clear that stents can be constructed in many different ways. The present invention is applicable to all known stent constructions, and it will be readily apparent from the following discussion of several exemplary constructions how the invention can be applied to any other type of stent construction.

Figure 1:
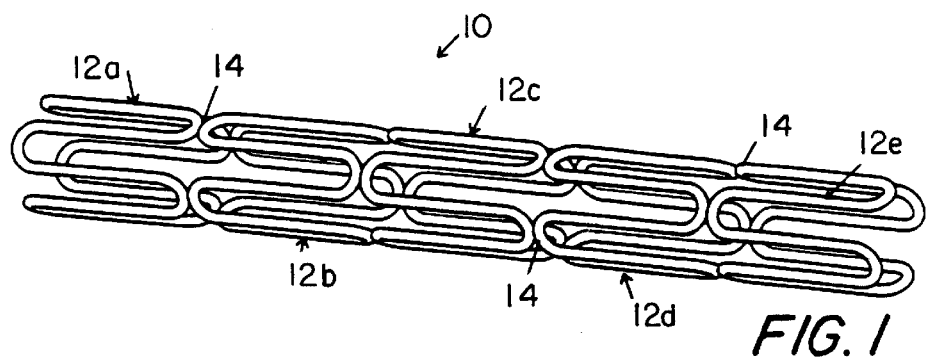
FIG. 1 is a simplified isometric view of an illustrative embodiment of a stent constructed in accordance with this invention.

An illustrative stent 10 made of metal is shown in FIG. 1. Stent 10 includes five sections 12a–e, each of which is made of an endless metal loop that has been bent so that it no longer lies in a plane (see, for example, the above-mentioned Boneau patent for more detail as to how each of sections 12 may be shaped). As the Boneau patent makes clear, each section 12 may have more undulations than are shown in FIG. 1 (and generally similar subsequent FIGS.), but the simplified depictions shown herein will be sufficient to illustrate the present invention. Although sections 12 may or may not be made of what would be regarded in some other arts as wire, the material of sections 12 is generally wire-like, and so the term "wire" is sometimes used herein to refer to such stent material. Axially adjacent sections 12 may be joined to one another as indicated at regions 14 (only representative ones of which have the reference number 14 in FIG. 1). These connections (if and to the extent present) may be made by welding, soldering, adhesive bonding, mechanical fastening, or in any other suitable way.

A typical technique for applying stents of the general type shown in FIG. 1 is to initially dispose the stent structure in a circumferentially compressed form (e.g., the form shown in FIG. 1) around a deflated balloon which is part of a balloon catheter. The catheter is then inserted axially into a tubular body structure to be stented until the balloon and stent are at the desired location along the body structure. Then the balloon is inflated to circumferentially expand the stent. Lastly, the balloon is deflated and the catheter is withdrawn, leaving the expanded stent behind in the body structure.

The deformation of the stent produced by the balloon as described above is at least partly permanent. (For convenience herein and in the appended claims, such permanent deformation will be referred to as "plastic". It will be understood that the terms "plastic", "plastically", or the like as used herein mean any type of non-elastic or permanent deformation, whether in the traditional materials science sense and therefore due to straining some portion of the stent material beyond its elastic limit, or as a result of any other property of the stent material or structure which results in the deformed stent taking a "set" which is different from its initial set. Correspondingly, the term "yield strength" or the like as used herein and in the appended claims means the point at which the stent structure or its material transitions from elastic to plastic deformation, as the term "plastic" is broadly defined above.) The balloon is strong enough to overcome the yield strength of the stent, but when the balloon is no longer radially supporting the stent, the surrounding tubular body structure does not exert enough radially inward force on the stent to take it back through its yield point, at least not to the extent that the stent returns to its original diameter.

Figure 2:
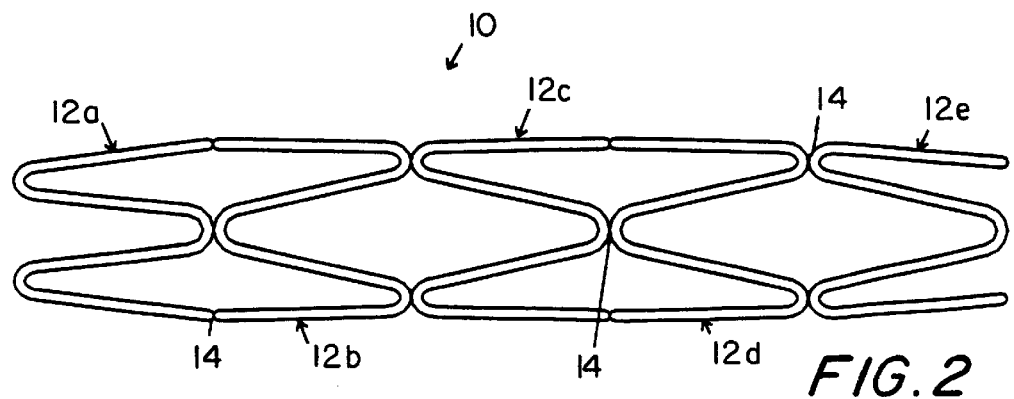
FIG. 2 is a simplified elevational view of the stent of FIG. 1 after circumferential expansion and implantation in a tubular body structure.

In accordance with the present invention, at least one axial end section 12*a* or 12*e* of stent 10 is made so that it holds open ("stents") the surrounding portion of the tubular body structure somewhat less strongly and/or somewhat less extensively than the remaining sections of the stent. In other words, at least one of stent sections 12*a* and 12*e* stents the surrounding portion of the tubular body organ to a lesser degree than other sections 12 of stent 10. This can be accomplished in many different ways. For example, the less strongly stenting axial end section 12*a* or 12*e* can be made from a material having a lower modulus of elasticity or spring force than the other sections. Then, after the stent has been circumferentially expanded and released, the axial end section 12*a* or 12*e* holds open its radially adjacent or surrounding portion of the tubular body structure less strongly and/or less extensively than the other sections of the stent hold open their radially adjacent or surrounding body structure portions. FIG. 2 shows how the stent of FIG. 1, constructed as has just been described, appears when circumferentially expanded and released in a tubular body structure. FIG. 2 illustrates the case in which both end sections 12*a* and 12*e* are made less strongly stenting than other sections of the stent.

The latter portion of the preceding paragraph describes making axial end section 12*a* or 12*e* elastically weaker than the other sections. A similar result can be achieved by making axial end section 12*a* or 12*e* plastically weaker (i.e., of lower yield strength) than other sections, so that after the stent has been implanted in a tubular body structure, the body structure can plastically recompress the weaker axial end section more than it plastically recompresses the other sections. For example, this can be done by using materials with different yield strengths for the various stent sections and/or by using a plastically weaker configuration or construction for end section 12*a* or 12*e*. The sections other than 12*a* or 12*e* may have sufficiently high yield strength that they are not plastically recompressed at all. In that case the tubular body structure only exceeds the lower yield strength of the relatively weak end section 12*a* or 12*e*. (It will be understood, of course, that the tubular body structure typically elastically recompresses all sections of the stent in addition to the above-described plastic deformation of (at least) end section 12*a* or 12*e*.) Although less strong than the other sections of the stent, end section 12*a* or 12*e* is nevertheless strong enough to hold open the tubular body structure to some degree more than it was open prior to stenting. Again, FIG. 2 shows how the stent of FIG. 1, constructed as described in this paragraph, appears when circumferentially expanded and released in a tubular body structure. As mentioned above, FIG. 2 illustrates the case in which both end sections 12*a* and 12*e* are made less strongly stenting than other sections of the stent.

Stent sections having different yield strengths can be made in many different ways. For example, the various stent sections can be made of different materials which have different yield strengths. In the case of metal stents, the various sections can be annealed differently or to different degrees to give them different yield strengths. In particular, a lower yield strength axial end section 12*a* or 12*e* is annealed more than other sections. In the case of stents made of precipitation hardening materials, the various sections can be precipitation hardened by different amounts to give them different yield strengths. In particular, a lower yield strength end section 12*a* or 12*e* is precipitation hardened less than other sections. Annealing and precipitation hardening are further discussed in connection with the next illustrative embodiments to be described. As an alternative to using different materials or differently treated materials to produce stent section 12 with different yield strengths, the configuration or construction of the various sections can be made different so that end section 12*a* or 12*e* yields more easily than other sections. For example, end section 12*a* or 12*e* can be made from thinner wire or can be made axially longer so that it is not strong enough to escape some plastic re-deformation when it is released by the balloon and therefore circumferentially recompressed by the tubular body structure.

As another example of stents in accordance with this invention, axial end section 12*a* or 12*e* may be made with a higher yield strength than the other sections. Then, when the stent is circumferentially expanded and released, the higher yield strength end section 12*a* or 12*e* tends to recoil from the circumferential expansion somewhat more than the lower yield strength sections. The higher yield strength end section 12*a* or 12*e* therefore holds open the surrounding portion of the stented body structure less extensively than the lower yield strength sections hold open their surrounding portion of the body structure. Once again, this is shown in FIG. 2 (for the case in which both axial end sections 12*a* and 12*e* have higher yield strength than medial sections 12*b–d*) by the somewhat smaller average diameters of axial end sections 12*a* and 12*e* as compared to the diameters of the medial sections 12b–d. In embodiments of this kind, even the lower yield strength sections are preferably strong enough to avoid plastic recompression by the tubular body structure when the balloon is deflated and removed.

A difference in material that can be used to produce an end section of higher yield strength may be just a different treatment of the material. In the case of metal stents, for example, the axial end section may be annealed less than other sections of the stent. Precipitation hardening materials may be used to produce an effect somewhat opposite to annealing. With such materials, the longer the material is "aged" (i.e., held at an elevated temperature that causes precipitation of hardening constituents in the material) the higher the yield strength of the material becomes. Thus axial end section 12a or 12e may be the aged section (or the section that is aged more than the other sections) to give it a higher yield strength. The result is similar to that described above in connection with FIG. 2.

Figure 3:
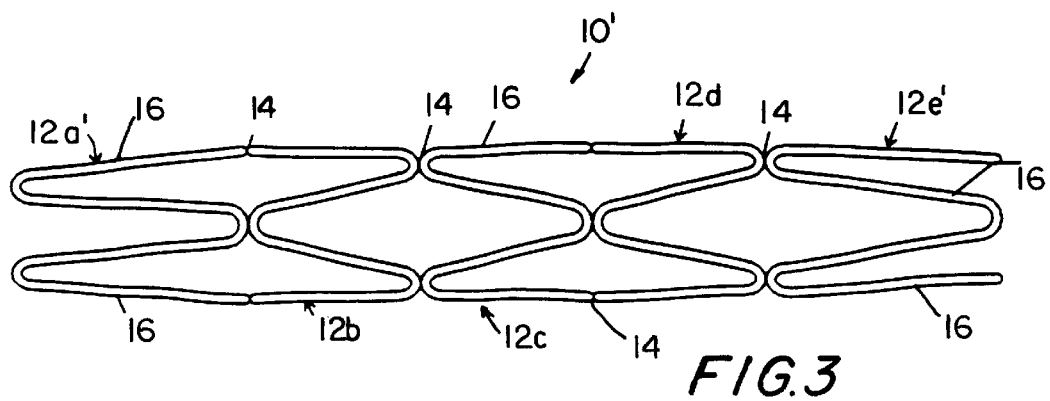
FIG. 3 is another view similar to FIG. 2 showing another illustrative embodiment of the invention. Like FIG. 2.

Other ways to produce less strongly stenting axial end sections 12a or 12e in accordance with this invention include making axial end section 12a or 12e from thinner and therefore less strong wire than the other sections. Thus axial end section 12a or 12e may be elastically and/or plastically recompressed by the tubular body structure more than other sections are elastically and/or plastically recompressed by that body structure. Or axial end section 12a or 12e may be made with a different configuration, which is selected to be circumferentially weaker (plastically or elastically) than the other sections. FIG. 3 shows an example of this approach, in which both axial end sections 12a' and 12e' are made longer than sections 12b–d. The longer segments 16 of wire in sections 12a' and 12e' are more easily deflected, thereby giving axial end sections 12a' and 12e' less circumferential strength than the other sections 12b–d. Varying the number of undulations from section to section is another way to provide the various sections with different stenting strengths. Varying the structure in a tubular slotted stent design or the structural shape in other stent designs can also be used to produce end sections which either spring back more after circumferential expansion and release, or which provide less strength of support, or both.

As has been alluded to, FIGS. 2 and 3 explicitly illustrate the point that both axial end sections 12a and 12e (now and hereafter used as generic references for the axial end sections in any of the depicted embodiments) can be made as described above for either axial end section. Indeed, the presently preferred embodiments are those in which both axial end sections 12a and 12e are made less strongly stenting than the remaining medial sections 12b–d.

By providing at least one and preferably two axial end sections that are less strongly stenting than the other sections, the transition or transitions between the stented and unstented portions of the tubular body structure are made less abrupt. This helps make the stent more acceptable to the body and therefore less likely to produce an adverse reaction in the body.

It will be understood that the principles described above are equally applicable to all other types of stent constructions. For example, these principles can be applied to tubular slotted stents, to tubular braided wire stents, to self-expanding stents, to thermally expanding stents, to non-metallic (e.g., polymeric, ceramic, and/or composite) stents, etc. It will be readily apparent to those skilled in the art how the principles of this invention can be applied to all of these various types of stents. For example, weaker end sections can be produced in polymeric and/or ceramic stents by variations in material properties, material condition, and/or structural shape.

As another example of modifications within the scope of this invention, stent sections with more than two different degrees of stenting can be used if desired. Thus the degree of stenting of sections 12b and 12d in FIG. 1 could be greater than the degree of stenting of sections 12a and 12e, but less than the degree of stenting of section 12c, to provide a stent which gradually increases in degree of stenting (i.e., circumferential strength and/or extent) from either axial end toward the center. The number of sections 12 shown in the drawings is merely illustrative, and any number of sections can be used. The sections may be connected to one another or not, as desired. The sections need not be discrete, but could instead be portions of one continuous structure whose degree of stenting varies stepwise or gradually (e.g., continuously) along its axial length. Thus it will be understood that references herein to stent portions or sections being "axially spaced" from one another do not require these stent portions or sections to be at some axial distance from one another. Rather, they can be immediately adjacent to one another if desired. "Axially spaced" merely means that the stent portions or sections form a succession along the longitudinal axis of the stent or the tubular body structure in which the stent is used.

The invention claimed is:

1. A method of implanting an axially extending annular stent in a tubular body structure to radially support the tubular body structure, said stent having first and second axially spaced portions such that said first portion is circumferentially stronger than said second portion, said method comprising the steps of:

inserting said stent in said tubular body structure;

circumferentially expanding said stent so that it must support itself and said tubular body structure and so that said tubular body structure is able to circumferentially recompress said second portion more than said first portion; and forming said first portion from a material that is stronger than a material from which said second portion is formed.

2. The method defined in claim 1 wherein said forming step comprises the step of:

employing for said first portion a material having a higher modulus of elasticity than the material from which said second portion is formed.

3. The method defined in claim 1 wherein said forming step comprises the step of:

employing for said first portion a material having a higher yield strength than the material from which said second portion is formed.

4. The method defined in claim 3 wherein the material of said stent is metal, and wherein said employing step comprises the step of:

annealing the metal of said second portion to a greater degree than the metal of said first portion is annealed.

5. The method defined in claim 3 wherein the material of said stent is precipitation hardening material, and wherein said employing step comprises the step of:

precipitation hardening the material of said first portion to a greater degree than the material of said second portion is precipitation hardened.

6. A method of implanting an axially extending annular stent in a tubular body structure to radially support the tubular body structure, said stent having first and second axially spaced portions such that said first portion is circumferentially stronger than said second portion, said method comprising the steps of:

inserting said stent in said tubular body structure;

circumferentially expanding said stent so that it must support itself and said tubular body structure and so that said tubular body structure is able to circumferentially recompress said second portion more than said first portion; and forming said first portion from a member having a larger cross section than a member from which said second portion is formed.

7. A method of implanting an axially extending annular stent in a tubular body structure to radially support the tubular body structure, said stent having first and second axially spaced portions such that said first portion is circumferentially stronger than said second portion, said stent being capable of being compressed onto a catheter, said method comprising the steps of:

compressing said stent onto a catheter;

inserting said stent in said tubular body structure;

forcibly expanding said stent such that said stent must support itself and said tubular body structure and so that said tubular body structure is able to circumferentially recompress said second portion more than said first portion; and forming said first portion from members that are shorter between connections to other members than members from which said second portion is formed.

8. The method of implanting an axially extending annular stent in a tubular body structure to radially support the tubular body structure, said stent having first and second axially spaced portions such that said second portion has a higher yield strength than said first portion, said method comprising the steps of:

inserting said stent in said tubular body structure;

circumferentially expanding said stent; and releasing said stent so that it must support itself and said tubular body structure and so that said second portion springs back more from circumferential expansion than said first portion.

9. The method defined in claim 8 wherein said stent is made of metal, and wherein said method further comprises the step of:

forming said first portion from metal that is annealed to a greater degree than the metal from which said second portion is formed.

10. The method defined in claim 8 wherein said stent is made of precipitation hardening material, and wherein said method further comprises the step of:

forming said second portion from material that is precipitation hardened to a greater degree than the material from which said first portion is formed.

11. The method defined in claim 8 wherein said stent also has a third portion axially spaced from said second portion by said first portion, said third portion also having a higher yield strength than said first portion, and wherein said releasing step comprises the step of releasing said third portion so that said third portion springs back more from circumferential expansion than said first portion.

* * * * *